US011192843B2

(12) United States Patent
Badgandi et al.

(10) Patent No.: US 11,192,843 B2
(45) Date of Patent: Dec. 7, 2021

(54) PROCESS FOR PRODUCING METHANOL

(71) Applicant: SABIC GLOBAL TECHNOLOGIES B.V., Bergen op Zoom (NL)

(72) Inventors: Srikant Vasant Badgandi, Bangalore (IN); Balasubramaniyan Sethuraman, Bangalore (IN); Vinod Sankaran Nair, Bangalore (IN)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 17/265,306

(22) PCT Filed: Aug. 5, 2019

(86) PCT No.: PCT/IB2019/056646
§ 371 (c)(1),
(2) Date: Feb. 2, 2021

(87) PCT Pub. No.: WO2020/031063
PCT Pub. Date: Feb. 13, 2020

(65) Prior Publication Data
US 2021/0300849 A1 Sep. 30, 2021

Related U.S. Application Data

(60) Provisional application No. 62/715,194, filed on Aug. 6, 2018.

(51) Int. Cl.
*C07C 29/151* (2006.01)
*C01C 1/04* (2006.01)

(52) U.S. Cl.
CPC ............ *C07C 29/1518* (2013.01); *C01C 1/04* (2013.01); *C01B 2203/0495* (2013.01);
(Continued)

(58) Field of Classification Search
CPC .................. C07C 29/1518; C01C 1/04; C01B 2203/0495; C01B 2203/061;
(Continued)

(56) References Cited

U.S. PATENT DOCUMENTS 4,886,651 A 12/1989 Patel et al.
5,180,570 A 1/1993 Lee et al.
(Continued)

FOREIGN PATENT DOCUMENTS

GB 2539521 12/2016
WO WO 2003/018958 3/2003
(Continued)

OTHER PUBLICATIONS

International Search Report and Written Opinion issued in Corresponding PCT Application No. PCT/IB2019/056646, dated Dec. 19, 2019.

*Primary Examiner* — Jafar F Parsa
(74) *Attorney, Agent, or Firm* — Norton Rose Fulbright US LLP

(57) ABSTRACT

A method for producing methanol is disclosed. The method includes supplying a high oxygen content oxidant to combust hydrocarbons, in particular methane, and then using the resulting hot gases to heat natural gas so as to convert the natural gas to synthesis gas. The synthesis gas is used to produce methanol in a methanol synthesis reactor. At least some of the carbon dioxide from the hot gases is fed to the methanol synthesis reactor to make methanol.

20 Claims, 3 Drawing Sheets

(52) U.S. Cl.
CPC .. *C01B 2203/061* (2013.01); *C01B 2203/068* (2013.01); *C01B 2203/0816* (2013.01); *C01B 2203/0822* (2013.01); *C01B 2203/1241* (2013.01); *C01P 2006/82* (2013.01)

(58) Field of Classification Search
CPC ...... C01B 2203/1241; C01B 2203/068; C01B 2203/0816; C01B 2203/0822
See application file for complete search history.

(56) References Cited

U.S. PATENT DOCUMENTS

| | | |
|---|---|---|
| 6,632,846 B2 | 10/2003 | Sheppard et al. |
| 6,881,758 B2 | 4/2005 | Guillard et al. |
| 7,300,642 B1 | 11/2007 | Pedersen et al. |
| 7,803,329 B2 | 9/2010 | Pedersen et al. |
| 8,769,961 B2 | 7/2014 | Allam |
| 8,772,360 B2 | 7/2014 | Allam |
| 9,169,778 B2 | 10/2015 | Allam |
| 9,260,303 B2 | 2/2016 | Filippi et al. |
| 2014/0100391 A1* | 4/2014 | Olah ................ C07C 41/09 568/698 |
| 2016/0083260 A1 | 3/2016 | Dahl |
| 2016/0107890 A1 | 4/2016 | Allam |

FOREIGN PATENT DOCUMENTS

| | | |
|---|---|---|
| WO | WO 2014/058549 | 4/2014 |
| WO | WO 2016/071061 | 5/2016 |

\* cited by examiner

PROCESS FOR PRODUCING METHANOL

CROSS REFERENCE TO RELATED APPLICATIONS

This application is a national phase under 35 U.S.C. § 371 of International Application No. PCT/IB2019/056646, filed Aug. 5, 2019, which claims the benefit of priority to U.S. Provisional Patent Application Ser. No. 62/715,194, filed Aug. 6, 2018, the entire contents of each of which are hereby incorporated by reference in their entirety.

FIELD OF INVENTION

The present invention generally relates to the production of methanol. More specifically, the present invention relates to the production of methanol by a process that includes using carbon dioxide ($CO_2$), from a heating medium that provides heat to a reforming process, as one of the raw materials in the production of the methanol.

BACKGROUND OF THE INVENTION

One conventional method of producing methanol includes producing synthesis gas from methane and then reacting the carbon monoxide (CO), the hydrogen ($H_2$), and the synthesis gas, in the presence of a catalyst to produce the methanol. The formula for the steam reforming of methane to form synthesis gas and the formula for the reaction of carbon monoxide and hydrogen to form methanol are shown below.

$$CH_4 + H_2O \rightarrow CO + 3H_2$$

$$CO + 2H_2 \rightarrow CH_3OH.$$

Conventionally, methanol producing plants utilize excess air in reformer burners to combust natural gas (fuel) to generate the required energy for steam reforming of natural gas (raw material) to form synthesis gas. In steam reforming methane to produce synthesis gas, for every mole of carbon monoxide formed, three moles of hydrogen are formed. But in the formation of methanol, for every mole of carbon monoxide consumed, only two moles of hydrogen are consumed. Thus, the steam reforming produces an excess of hydrogen. The excess hydrogen produced in steam reforming is utilized for methanol production by importing carbon dioxide and reacting the imported carbon dioxide with the excess hydrogen to form the methanol as shown below.

$$CO_2 + 3H_2 \rightarrow CH_3OH + H_2O.$$

This method of consuming the excess hydrogen is expensive and increases the production cost of methanol because of the high price to import carbon dioxide.

Moreover, the use of the excess air to burn fuel gas results in other significant inefficiencies. For example, currently, the use of excess air in reformer burners for combustion results in a diluted carbon dioxide stream comprising of about 5 wt. % $CO_2$, 80 wt. % $N_2$ and 15 wt. % $O_2$. This dilute stream is very difficult to process further so it is vented as flue gas. Also, using excess air in the burners of reformers will reduce the burner flame temperatures, thereby increasing the natural gas demand as fuel for reformer burners. In summary, the use of excess air in combusting natural gas fuel and importing excess carbon dioxide to consume excess hydrogen makes the methanol production process expensive.

In view of the venting of the flue gas that includes carbon dioxide mentioned above, it should be noted that the emission of carbon dioxide from industrial plants is an environmental concern. Carbon dioxide is a greenhouse gas that is continuously being emitted into the Earth's atmosphere, primarily as a result of the burning of fossil fuels. Over the last few decades, there has been an increasing global concern over the rise of anthropogenic carbon dioxide emission into the atmosphere.

BRIEF SUMMARY OF THE INVENTION

The present inventors have discovered a more efficient and environmentally friendly method for the production of methanol from synthesis gas. The method involves the in-situ formation of carbon dioxide, which can then be used as additional raw material for producing methanol and/or other valuable chemicals such as urea. The method includes providing an oxidant that is pure oxygen or has a high concentration of oxygen for the burning of fuel in the burner of the reformer that produces the synthesis gas. The oxidant can be produced from air by an air separation unit (ASU). This oxidant is used to burn the fuel completely or almost completely in the burner, thereby reducing fuel consumption and increasing synthesis gas production in the reformer (e.g., a steam reformer). Excess carbon dioxide that results from the use of the high oxygen content oxidant is used as one of the raw materials in producing methanol and urea. Nitrogen from the air separation unit and any unreacted hydrogen from the reformer can be used to produce materials such as ammonia and urea. The method can significantly optimize a methanol plant and result in increased economic benefit. For example, although carbon dioxide is utilized in this method, that carbon dioxide is not imported to the methanol production process. Instead, the method includes producing pure carbon dioxide (or almost pure carbon dioxide) in-situ from burner flue gas. In this way, carbon dioxide that would normally be emitted to the atmosphere can be used in forming valuable products such as methanol and urea.

Embodiments of the invention include a method of producing methanol. The method includes combusting feed hydrocarbons with an oxidant that comprises 70 to 99.5 wt. % oxygen to generate heat and produce a heated gas stream at a temperature of 1200 to 1800° C. The heated gas stream comprises carbon dioxide and water. The method further includes heating natural gas, with heat from the heated gas stream, to a temperature sufficient to reform the natural gas and produce synthesis gas. The heating of the natural gas concurrently cools the heated gas stream to form a cooled gas stream comprising carbon dioxide and water. The method also includes reacting the synthesis gas and at least some of the carbon dioxide from the cooled gas stream under reaction conditions sufficient to produce methanol.

Embodiments of the invention include a method of producing methanol that involves separating a methane stream into a first methane stream and a second methane stream and flowing the first methane stream to a burner. The method further includes separating air, in an air separation unit, to produce an oxidant that comprises 70 to 99.5 wt. % oxygen, 1 to 30 wt. % carbon-dioxide (blended to act as a temperature moderator), and 0.1 to 5 wt. % nitrogen, along with trace impurities. The method also includes flowing the oxidant to the burner and combusting the first methane stream with the oxidant, along with carbon dioxide generated from natural gas combustion (which is used to control the flame temperature), to generate heat and produce a heated gas stream at a temperature of 1200 to 1800° C. The heated gas stream comprises carbon dioxide and water (in the form of steam). The method further includes contacting the heated gas stream with a reformer and flowing the second methane stream to the reformer. The method also includes heating the second methane stream, with heat from the heated gas stream, to a temperature sufficient to reform the second methane stream and produce synthesis gas. The heating of the second methane stream concurrently cools the heated gas stream to form a cooled gas stream comprising carbon dioxide. The method further includes flowing the synthesis gas to a methanol synthesis reactor, flowing at least some of the carbon dioxide of the cooled gas stream to the methanol synthesis reactor, and reacting, in the methanol synthesis reactor, the synthesis gas and at least some of the carbon dioxide of the cooled gas stream under reaction conditions sufficient to produce methanol.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for the production of methanol from synthesis gas. The method involves the in-situ production of carbon dioxide, which can then be used as additional raw material for producing methanol and/or other valuable chemicals such as urea. The method includes providing an oxidant that is pure oxygen or has a high concentration of oxygen for the burning of fuel in the burner of a reformer that produces the synthesis gas. The oxidant can be produced from air by an air separation unit (ASU). This oxidant is used to burn the fuel completely, or almost completely, in the burner, thereby reducing fuel consumption and increasing synthesis gas production in the reformer. With the use of this high oxygen content oxidant for burning the fuel, burner flue gas will include excess carbon dioxide and water. The carbon dioxide can be easily separated from the water and then utilized as raw material with hydrogen to produce valuable product such as methanol. In this way, the excess hydrogen is consumed by reaction with carbon dioxide to form methanol.

The method, according to embodiments of the invention, can be used to optimize a methanol plant by using an air separation unit to obtain pure oxygen or almost pure oxygen as the oxidant, which can be used to completely burn fuel natural gas in the burner to produce carbon dioxide and water. A large percentage of the carbon dioxide in the burner flue gas can be recovered by separating water using compression and condensation processes. Purified carbon dioxide can then be internally utilized in the methanol converter to consume excess hydrogen produced in the steam reforming of natural gas.

Embodiments of the invention present a possibility of integration of the methanol production process with ammonia and urea production processes as nitrogen is produced as a by-product in the air separation unit, excess carbon dioxide is available from the burner flue gas (blended to act as a temperature moderator), and excess hydrogen is available from steam reforming of natural gas.

As noted above, conventional methanol plants utilize excess air in reformer burners to combust fuel gas to generate the required energy for steam reforming (which results in significant energy inefficiencies) and import pure carbon dioxide to consume excess hydrogen produced in the reforming section. This importation of carbon dioxide makes the conventional process economically unattractive.

Figure 1:
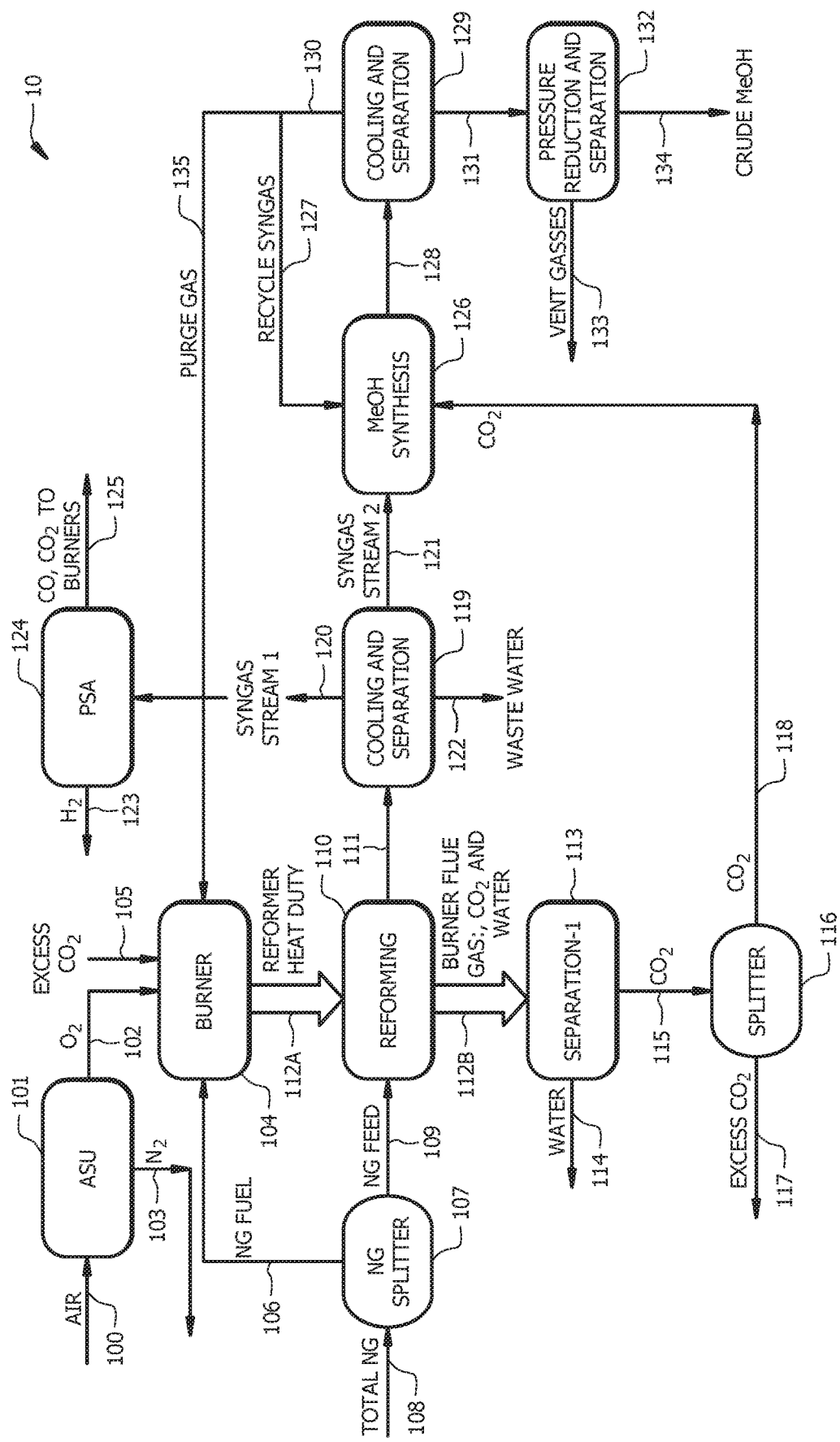
FIG. 1 is a system for producing methanol, according to embodiments of the invention.
Figure 2:
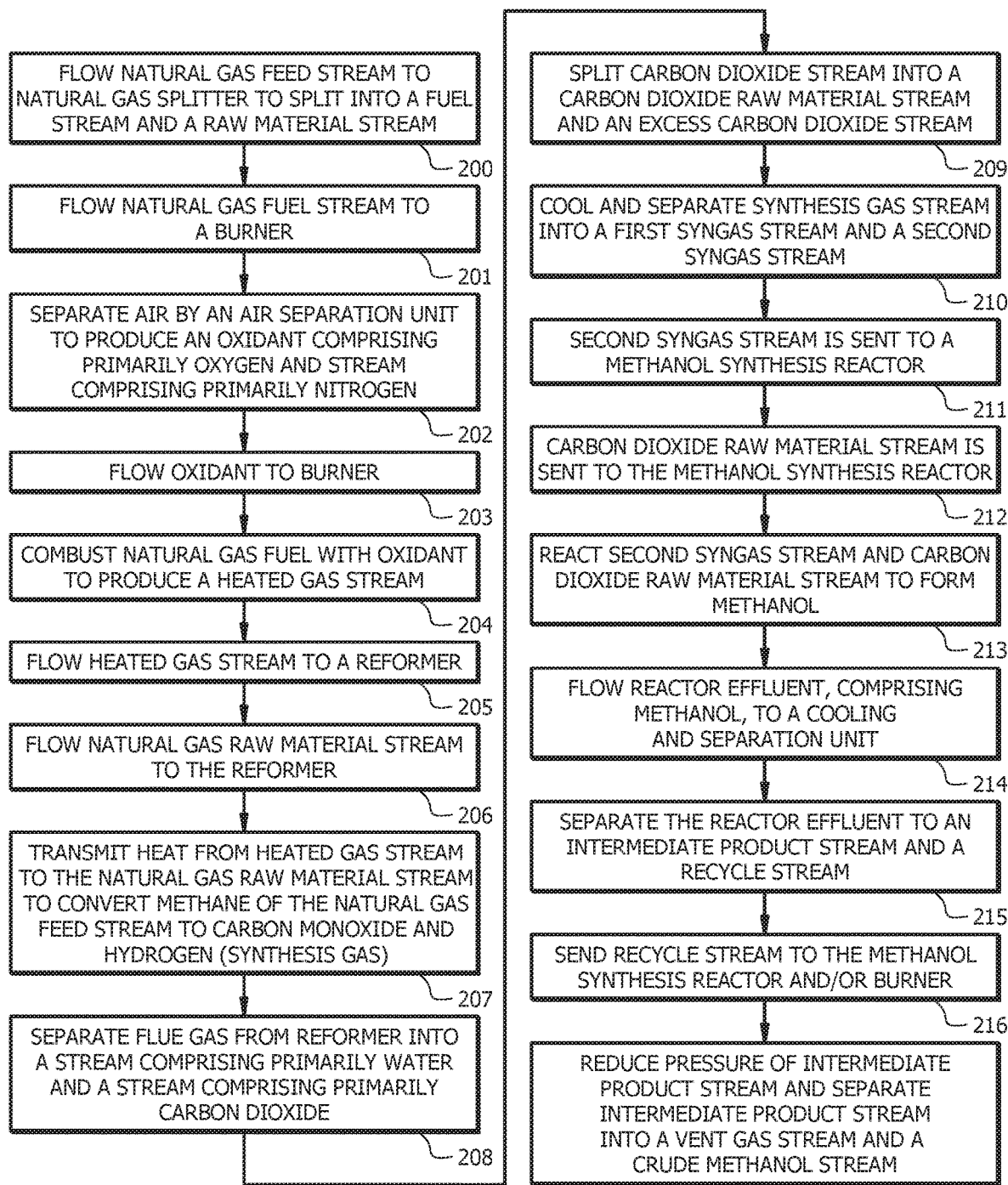
FIG. 2 is a method for producing methanol, according to embodiments of the invention.

FIG. 1 shows system 10 for producing methanol, according to embodiments of the invention. FIG. 2 shows method 20 for producing methanol, according to embodiments of the invention. Method 20 may be implemented by using system 10.

Method 20, as implemented using system 10, may involve, at block 200, flowing natural gas feed stream 108 to natural gas splitter 107, which splits natural gas feed stream 108 into natural gas fuel stream 106 and natural gas feed stream 109. In this way, the methane of the natural gas serves as both fuel and raw material. Natural gas comprises primarily methane and in embodiments of the invention the natural gas comprises 70 to 100 wt. % methane, 0 to 30 wt. % ethane, 0 to 10 wt. % nitrogen and 0 to 10 wt. % propane on dry basis.

In embodiments of the invention, method 20 includes flowing natural gas fuel stream 106 to burner 104 for combusting, at block 201. Concurrently, according to embodiments of the invention, at block 202, air stream 100 is separated by air separation unit 101 into oxidant stream 102 and nitrogen stream 103. Oxidant stream 102, according to embodiments of the invention, comprises 70 to 99.5 wt. % oxygen, 1 to 30 wt. % carbon dioxide (blended to act as a temperature moderator), and 0.1 to 5 wt. % nitrogen, along with trace impurities; and nitrogen stream 103 comprises 70 to 90 wt. % nitrogen and 10 to 30 wt. % oxygen. Because $CO_2$ has a very high radiation absorption coefficient it can act as a temperature diffuser near a flame of burning natural gas. Also, $CO_2$ is an inert component in an oxygen rich environment which helps in absorbing some exothermic energy of combustion at the flame region due to its sensible heating. Hence, $CO_2$ blending composition can be optimized based on the desired flame temperature.

Oxidant stream 102, having high oxygen content, is flowed to burner 104, at block 203. At block 204, according to embodiments of the invention, burner 104 burns natural gas fuel 106 with oxidant stream 102. Because of the high oxygen content of oxidant stream 102, the burning of natural gas fuel stream 106 can be complete or almost complete. According to embodiments of the invention, the combusting at block 204 results in the oxidation of at least 95 to 100% of the hydrocarbons fed to burner 104. In this way, natural gas (fuel) consumption is reduced and synthesis gas production is increased in reformer 110 (e.g., a steam reforming unit).

In embodiments of the invention, at block 204, carbon dioxide stream 105 is provided to burner 104 while methane of natural gas fuel stream 106 is combusted with oxygen of oxidant stream 102 in burner 104. In this way, carbon dioxide stream 105, which is an inert gas in the conditions existing in burner 104, can be used to control the flame temperature in burner 104. In embodiments of the invention, the flame temperature is in a range of 1500 to 3000° C. and all ranges and values there between including ranges of 1300 to 1350° C., 1350 to 1400° C., 1400 to 1450° C., 1450 to 1500° C., 1500 to 1550° C., 1550 to 1600° C., 1600 to 1650° C., 1650 to 1700° C., 1700 to 1750° C., 1750 to 1800° C., 1800 to 1850° C., 1850 to 1900° C., 1900 to 1950° C., 1950 to 2000° C., 2000 to 2050° C., 2050 to 2100° C., 2100 to 2150° C., 2150 to 2200° C., 2200 to 2250° C., 2250 to 2300° C., 2300 to 2350° C., 2350 to 2400° C., 2400 to 2450° C., 2450 to 2500° C., 2500 to 2550° C., 2550 to 2600° C., 2600 to 2650° C., 2650 to 2700° C., 2700 to 2750° C., 2750 to 2800° C., 2800 to 2850° C., 2850 to 2900° C., 2900 to 2950° C., and/or 2950 to 3000° C.

The burning at block 204, in burner 104, produces heat duty stream 112A (a heated gas stream). Heat duty stream 112A, in embodiments of the invention, may be heated to a temperature of 1200 to 1800° C. and all ranges and values there between including ranges of 1200 to 1250° C., 1250 to 1300° C., 1300 to 1350° C., 1350 to 1400° C., 1400 to 1450° C., 1450 to 1500° C., 1500 to 1550° C., 1550 to 1600° C., 1600 to 1650° C., 1650 to 1700° C., 1700 to 1750° C., and/or 1750 to 1800° C. Block 205 shows that heat duty stream 112A is routed to reformer 110, in embodiments of the invention.

In embodiments of the invention, at block 206, natural gas feed stream 109 is also flowed to reformer 110. At block 207, the heat that is produced by burning natural gas fuel stream 106 and that is present in heat duty stream 112A is transmitted to natural gas feed stream 109 to create a temperature sufficient to convert methane of natural gas feed stream 109 to the carbon monoxide and hydrogen of synthesis gas 111. In embodiments of the invention, the reaction conditions in reformer 110, at block 207, includes a temperature in a range of 800 to 900° C. and all ranges and values there between including ranges of 800 to 810° C., 810 to 820° C., 820 to 830° C., 830 to 840° C., 840 to 850° C., 850 to 860° C., 860 to 870° C., 870 to 880° C., 880 to 890° C., and/or 890 to 900° C. In embodiments of the invention, the reaction conditions in reformer 110, at block 207, includes a pressure in a range of 10 to 20 bar and all ranges and values there between including ranges of 10 to 11 bar, 11 to 12 bar, 12 to 13 bar, 13 to 14 bar, 14 to 15 bar, 15 to 16 bar, 16 to 17 bar, 17 to 18 bar, 18 to 19 bar, and/or 19 to 20 bar. In embodiments of the invention, the reactions at block 207 are carried out in the presence of a catalyst selected from the list consisting of: nickel, aluminum oxide, calcium oxide, and combinations thereof. At reformer 110, natural gas feed stream 109 is converted to synthesis gas 111. Synthesis gas 111 includes carbon monoxide and hydrogen. In embodiments of the invention, synthesis gas 111 comprises 15 to 25 wt. % carbon monoxide, 10 to 20 wt. % carbon dioxide, 5 to 15 wt. % hydrogen, and 40 to 50 wt. % water.

According to embodiments of the invention, the transmission of heat from heat duty stream 112A to natural gas feed stream 109 to create synthesis gas 111 causes heat duty stream 112A to cool to flue gas 112B, which comprises primarily carbon dioxide and water. Flue gas 112B comprises 70 to 80 wt. % carbon dioxide and 20 to 30 wt. % water, in embodiments of the invention.

The carbon dioxide and water of flue gas 112B can be easily separated. For example, in embodiments of the invention, at block 208, method 20 involves separation unit 113 separating flue gas 112B into a stream comprising primarily water (water stream 114) and a stream comprising primarily carbon dioxide (carbon dioxide stream 115).

In embodiments of the invention, carbon dioxide splitter 116, at block 209, splits carbon dioxide stream 115 into carbon dioxide raw material stream 118 and excess carbon dioxide stream 117. Excess carbon dioxide stream 117, in embodiments of the invention, is fed as carbon dioxide stream 105 into burner 104, as an aspect of block 204 and/or excess carbon dioxide stream 117 is injected into reformer 110. When supplied to burner 104, excess carbon dioxide stream 117, as an inert gas, acts as a diluent and thus can be used to control the flame temperatures of the burning natural gas fuel stream 106 in burner 104.

At block 210, according to embodiments of the invention, synthesis gas stream 111 is routed to cooling and separation unit 119, where synthesis gas stream 111 is cooled and separated into first syngas stream 120 and second syngas stream 121. In embodiments of the invention, first syngas stream 120 and second syngas stream 121 each comprises 30 to 40 wt. % carbon dioxide, 40 to 50 wt. % carbon monoxide, 10 to 20 wt. % hydrogen, and 0 to 10 wt. % water. First syngas stream 120 may be separated in pressure swing absorption (PSA) unit 124 to form hydrogen stream 123, comprising primarily hydrogen, and carbon oxide stream 125, which comprises primarily carbon dioxide and carbon monoxide.

At block 211, second syngas stream 121, according to embodiments of the invention, is routed to methanol synthesis reactor 126. At block 212, in embodiments of the invention, carbon dioxide raw material stream 118 is routed to methanol synthesis reactor 126, at block 212.

At block 213, according to embodiments of the invention, second syngas stream 121 and carbon dioxide raw material stream 118 are reacted and converted to methanol in methanol synthesis reactor 126. In embodiments of the invention, the reaction conditions provided in methanol synthesis reactor 126 for block 213—the synthesis of methanol from carbon monoxide, carbon dioxide, and hydrogen—include a temperature in a range of 225 to 275° C. and all ranges and values there between including ranges of 225 to 230° C., 230 to 235° C., 235 to 240° C., 240 to 245° C., 245 to 250° C., 250 to 255° C., 255 to 260° C., 260 to 265° C., 265 to 270° C., and/or 270 to 275° C. In embodiments of the invention, the reaction conditions in methanol synthesis reactor 126 for the synthesis of methanol, at block 213, includes a pressure in a range of 80 to 100 bar and all ranges and values there between including ranges of 80 to 82 bar, 82 to 84 bar, 84 to 86 bar, 86 to 88 bar, 88 to 90 bar, 90 to 92 bar, 92 to 94 bar, 94 to 96 bar, 96 to 98 bar, and/or 98 to 100 bar. In embodiments of the invention, the methanol synthesis reactions at block 213 are carried out in the presence of a catalyst selected from the list consisting of: copper, zinc oxide, aluminum oxide, and combinations thereof.

The methanol produced at block 213 is discharged in reactor effluent 128. In embodiments of the invention, reactor effluent 128 comprises 30 to 40 wt. % methanol, 10 to 20 wt. % carbon dioxide, 0 to 5 wt. % carbon monoxide, 10 to 20 wt. % hydrogen, and 10 to 20 wt. % water. Reactor effluent 128, according to embodiments of the invention, is sent to cooling and separation unit 129, at block 214. At block 215, in embodiments of the invention, cooling and separation unit 129 separates reactor effluent 128 into intermediate product stream 131 and recycle stream 130. Recycle stream 130, comprising primarily carbon dioxide and hydrogen, can be recycled to methanol synthesis reactor 126 as recycle synthesis gas 127 and/or recycled to burner 104 for burning as purge gas 135, as shown at block 216.

At block 217, in embodiments of the invention, pressure reduction and separation unit 132 reduces the pressure of intermediate product stream 131 and separates intermediate product stream 131 into vent gases stream 133 and crude methanol stream 134.

In embodiments of the invention, (1) at least a portion of excess carbon dioxide stream 117 can be integrated with an ammonia/urea plant for the production of urea and/or (2) hydrogen stream 123 and nitrogen stream 103 can be integrated with the ammonia/urea plant to produce ammonia. More specifically, nitrogen from nitrogen stream 103 can be reacted to hydrogen from hydrogen stream 123 or other hydrogen source to form ammonia. The formed ammonia can then be reacted with carbon dioxide of a portion of excess carbon dioxide stream 117 to form urea.

Embodiments of the invention as described herein can significantly optimize methanol production plants and result in increased economic benefit from using carbon dioxide to produce additional methanol, where the carbon dioxide is produced in-situ within reformer burners.

Embodiments of the invention as described herein can have the following benefits: (a) reduction of fuel natural gas consumption in the reformer burner as a result of using pure oxygen or oxidant with high concentration of oxygen for combustion, (b) in-situ production of pure carbon dioxide or almost pure carbon dioxide consumes the excess hydrogen produced in the reformer to produce additional methanol, (c) increased use of natural gas as a feedstock to generate additional synthesis gas, resulting in additional methanol production per unit of natural gas.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

Example

As part of the disclosure of the present invention, a specific example is included below. The example is for illustrative purposes only and is not intended to limit the invention. Those of ordinary skill in the art will readily recognize parameters that can be changed or modified to yield essentially the same results.

Simulation of Methanol Production Process

The example involves a first cut model (as shown in FIG. 1) in Aspen Plus Software built for carbon dioxide utilization in a methanol plant that results in additional methanol production from excess hydrogen in a synthesis gas stream entering the methanol synthesis reactor according to the reaction scheme below:

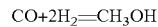

$CO+2H_2=CH_3OH$

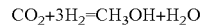

$CO_2+3H_2=CH_3OH+H_2O$

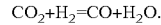

$CO_2+H_2=CO+H_2O.$

Assumptions in the simulation include: (a) total natural gas is fixed: 2788 kmol/hr or 415.1 kta, (b) natural gas split is varied based on the $CO_2$ injection so that energy balance is achieved between reformer and burner, (c) reforming and methanol synthesis are assumed to operate at equilibrium for this study, (d) all the calculations are relative to the base case of zero $CO_2$ injection, (e) net benefit is defined on a monetary basis (incremental methanol—make-up water—natural gas equivalent of steam)/ton of methanol relative to base case of no $CO_2$ injection.

Figure 3:
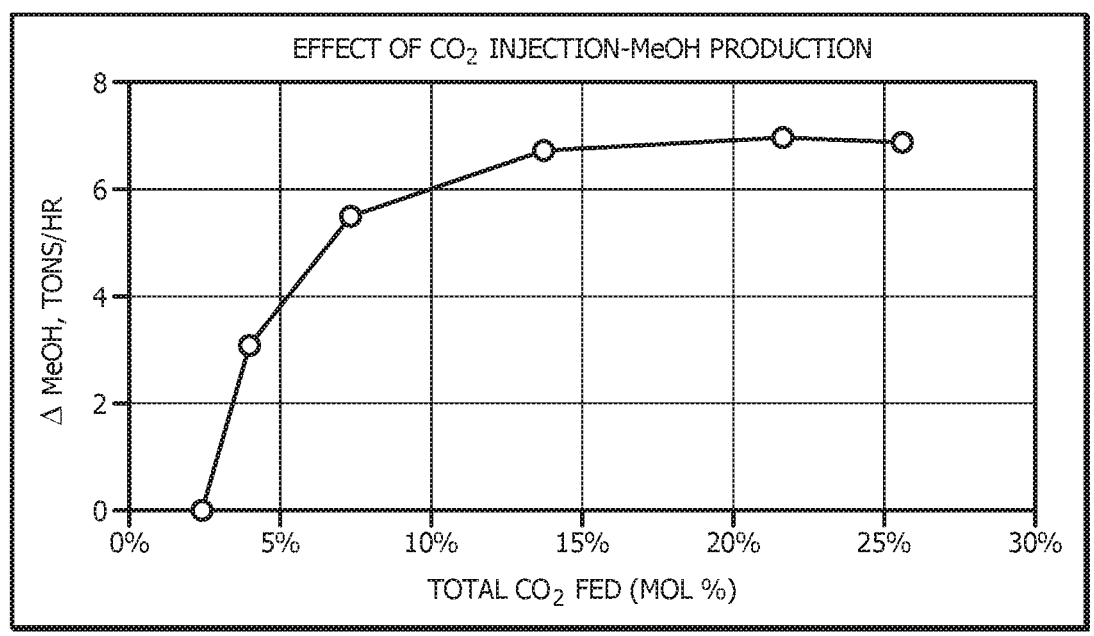
FIG. 3 shows a graph of results from a simulation of a method for producing methanol, according to embodiments of the invention.

Based on the simulation, results reflected in the graph shown in FIG. 3 were obtained. FIG. 3 shows that there is an increase in methanol produced per hour with an increase in carbon dioxide fed to the methanol synthesis reactor. Thus, there is a clear economic justification for injecting carbon dioxide in methanol synthesis reactors in order to generate additional methanol from excess hydrogen, which would otherwise be lost as a purge stream and ending up as a fuel in the reformer furnaces.

A preliminary comparison of the proposed idea versus the conventional process of methanol production is shown below:

| Operating Parameters | Conventional MeOH production Process | MeOH Production with Reformer using Pure Oxygen (Our IDEA) |
|---|---|---|
| Flame Temperature, Deg C. | X | 1.20 X |
| Natural Gas Consumption, tons/hr | X | 0.9 X |
| MeOH Increment, tons/hr | X | 1.10 X |
| Capex, $MM | X | 1.30 X |
| Syngas Ratio | X | X |
| Steam to Carbon Ratio | X | X |

Based on the above table, injection of pure oxygen offers considerable advantages in terms of natural gas savings as compared to conventional reformer for methanol production.

In the context of the present invention, at least the following 19 embodiments are described. Embodiment 1 is a method of producing methanol. The method includes combusting feed hydrocarbons with an oxidant that contains 70 to 99.5 wt. % oxygen to generate heat and produce a heated gas stream at a temperature of 1200 to 1800° C., wherein the heated gas stream contains carbon dioxide and water. The method also includes heating natural gas, with heat from the heated gas stream, to a temperature sufficient to reform the natural gas and produce synthesis gas, wherein the heating of the natural gas concurrently cools the heated gas stream to form a cooled gas stream containing carbon dioxide and water. The method further includes reacting the synthesis gas and at least some of the carbon dioxide from the cooled gas stream under reaction conditions sufficient to produce methanol. Embodiment 2 is the method of embodiment 1 further including separating air, in an air separation unit, to produce the oxidant. Embodiment 3 is the method of either of embodiments 1 or 2, where the air separation unit includes a selection from the list consisting of: a cryogenic distillation unit, a pressure swing adsorption/membrane separation unit, and combinations thereof. Embodiment 4 is the method of embodiment 3, further including producing ammonia and/or urea with raw materials that include nitrogen from the air separation unit. Embodiment 5 is the method of any of embodiments 1 to 4 further including separating carbon dioxide from water in the cooled gas stream and using the separated carbon dioxide for the reacting with the synthesis gas. Embodiment 6 is the method of any of embodiments 1 to 5 further including separating a methane stream into a first methane stream and a second methane stream, and flowing the first methane stream to a burner, wherein the first methane stream includes the feed hydrocarbons combusted with the oxidant. Embodiment 7 is the method of embodiment 6 further including flowing the heated gas stream to a reformer, and flowing the second methane stream to the reformer, wherein the second methane stream includes the natural gas that is heated. Embodiment 8 is the method of any of embodiments 1 to 7, wherein the oxidant further includes 1 to 30 wt. % carbon dioxide (blended to act as a temperature moderator), and 0.1 to 5 wt. % nitrogen. Embodiment 9 is the method of any of embodiments 1 to 8, wherein the combusting results in oxidation of 95 to 100 wt. % of the feed hydrocarbons. Embodiment 10 is the method of any of embodiments 1 to 9, wherein the cooled gas stream contains 55 to 65 wt. % carbon dioxide, 35 to 45 wt. % water, and 0.1 to 3 wt. % nitrogen. Embodiment 11 is the method of any of embodiments 1 to 10, wherein a portion of the carbon dioxide from the cooled gas stream is used in an ammonia and/or urea production process. Embodiment 12 is the method of any of embodiments 1 to 11, wherein a portion of the carbon dioxide from the cooled gas stream is used as a diluent in the combusting of the feed hydrocarbons. Embodiment 13 is the method of embodiment 12, wherein flow of the carbon dioxide from the cooled gas stream to the combusting of the feed hydrocarbons is varied to control flame temperature of the combusting. Embodiment 14 is the method of embodiment 13, wherein the flame temperature of the combusting is in a range of 1500 to 3000° C. Embodiment 14 is the method of any of embodiments 1 to 13, wherein conversion rate of natural gas to methanol is in a range of 70% to 95%. Embodiment 16 is the method of any of embodiments 1 to 15, wherein reforming the natural gas includes reacting the natural gas with water.

Embodiment 17 is a method of producing methanol. The method includes combusting a first methane stream methane with an oxidant that contains 70 to 99.5 wt. % oxygen to generate heat and produce a heated gas stream at a temperature of 1200 to 1800° C., wherein the heated gas stream contains carbon dioxide and water. The method also includes heating a second methane stream, with heat from the heated gas stream, to a temperature sufficient to reform the second methane stream and produce synthesis gas, wherein the heating of the second methane stream concurrently cools the heated gas stream to form a cooled gas stream containing carbon dioxide and water. The method further includes reacting the synthesis gas and at least some of the carbon dioxide from the cooled gas stream under reaction conditions sufficient to produce methanol.

Embodiment 18 is a method of producing methanol. The method includes separating a methane stream into a first methane stream and a second methane stream and flowing the first methane stream to a burner. The method also includes separating air, in an air separation unit, to produce an oxidant containing 70 to 99.5 wt. % oxygen, 1 to 30 wt. % carbon dioxide, and 0.1 to 5 wt. % nitrogen and flowing the oxidant to the burner. The method further includes combusting the first methane stream with the oxidant to generate heat and produce a heated gas stream at a temperature of 1200 to 1800° C., wherein the heated gas stream comprises carbon dioxide and water. In addition, the method includes flowing the heated gas stream to a reformer and flowing the second methane stream to the reformer. The method further includes heating the second methane stream, with heat from the heated gas stream, to a temperature sufficient to reform the second methane stream and produce synthesis gas, wherein the heating of the second methane stream concurrently cools the heated gas stream to form a cooled gas stream comprising carbon dioxide and flowing the synthesis gas to a methanol synthesis reactor. The method also includes flowing at least some of the carbon dioxide of the cooled gas stream to the methanol synthesis reactor and reacting, in the methanol synthesis reactor, the synthesis gas and at least some of the carbon dioxide of the cooled gas stream under reaction conditions sufficient to produce methanol. Embodiment 19 is the method of embodiment 18 wherein carbon dioxide generated from natural gas combustion is sent to a reaction zone of the combusting of the first methane stream.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of producing methanol, the method comprising:
combusting feed hydrocarbons with an oxidant that comprises 70 to 99.5 wt. % oxygen to generate heat and produce a heated gas stream at a temperature of 1200 to 1800° C., wherein the heated gas stream comprises carbon dioxide and water;
heating natural gas, with heat from the heated gas stream, to a temperature sufficient to reform the natural gas and produce synthesis gas, wherein the heating of the natural gas concurrently cools the heated gas stream to form a cooled gas stream comprising carbon dioxide and water; and
reacting the synthesis gas and at least some of the carbon dioxide from the cooled gas stream under reaction conditions sufficient to produce methanol.

2. The method of claim 1 further comprising:
separating air, in an air separation unit, to produce the oxidant.

3. The method of claim 1, where the air separation unit comprises a selection from the list consisting of: a cryogenic distillation unit, a pressure swing adsorption/membrane separation unit, and combinations thereof.

4. The method of claim 3, further comprising:
producing ammonia and/or urea with raw materials that include nitrogen from the air separation unit.

5. The method of claim 1 further comprising:
separating carbon dioxide from water in the cooled gas stream and using the separated carbon dioxide in the step of reacting the synthesis gas.

6. The method of claim 1 further comprising:
separating a methane stream into a first methane stream and a second methane stream; and
flowing the first methane stream to a burner, wherein the first methane stream comprises the feed hydrocarbons combusted with the oxidant.

7. The method of claim 6 further comprising:
flowing the heated gas stream to a reformer; and
flowing the second methane stream to the reformer, wherein the second methane stream comprises the natural gas that is heated.

8. The method of claim 1, wherein the oxidant further comprises 1 to 30 wt. % carbon dioxide, and 0.1 to 5 wt. % nitrogen.

9. The method of claim 1, wherein the combusting results in oxidation of 95 to 100 wt. % of the feed hydrocarbons.

10. The method of claim 1, wherein the cooled gas stream comprises 55 to 65 wt. % carbon dioxide, 35 to 45 wt. % water, 0.1 to 3 wt. % nitrogen.

11. The method of claim 1, wherein a portion of the carbon dioxide from the cooled gas stream is used in an ammonia and/or urea production process.

12. The method of claim 1, wherein a portion of the carbon dioxide from the cooled gas stream is used as a diluent in the combusting of the feed hydrocarbons.

13. The method of claim 12, wherein flow of the carbon dioxide from the cooled gas stream to the combusting of the feed hydrocarbons is varied to control flame temperature of the combusting.

14. The method of claim 13, wherein the flame temperature of the combusting is in a range of 1500 to 3000° C.

15. The method of claim 1, wherein conversion rate of natural gas to methanol is in a range of 70% to 95%.

16. The method of claim 1, wherein reforming the natural gas comprises reacting the natural gas with water.

17. A method of producing methanol, the method comprising:
combusting a first methane stream with an oxidant that comprises 70 to 99.5 wt. % oxygen to generate heat and produce a heated gas stream at a temperature of 1200 to 1800° C., wherein the heated gas stream comprises carbon dioxide and water;
heating a second methane stream, with heat from the heated gas stream, to a temperature sufficient to reform the second methane stream and produce synthesis gas, wherein the heating of the second methane stream concurrently cools the heated gas stream to form a cooled gas stream comprising carbon dioxide and water; and
reacting the synthesis gas and at least some of the carbon dioxide from the cooled gas stream under reaction conditions sufficient to produce methanol.

18. A method of producing methanol, the method comprising:
separating a methane stream into a first methane stream and a second methane stream;
flowing the first methane stream to a burner;
separating air, in an air separation unit, to produce an oxidant comprising 70 to 99.5 wt. % oxygen, 1 to 30 wt. % carbon dioxide, and 0.1 to 5 wt. % nitrogen;
flowing the oxidant to the burner;
combusting the first methane stream with the oxidant to generate heat and produce a heated gas stream at a temperature of 1200 to 1800° C., wherein the heated gas stream comprises carbon dioxide and water;
flowing the heated gas stream to a reformer;
flowing the second methane stream to the reformer;
heating the second methane stream, with heat from the heated gas stream, to a temperature sufficient to reform the second methane stream and produce synthesis gas, wherein the heating of the second methane stream concurrently cools the heated gas stream to form a cooled gas stream comprising carbon dioxide;
flowing the synthesis gas to a methanol synthesis reactor;
flowing at least some of the carbon dioxide of the cooled gas stream to the methanol synthesis reactor; and
reacting, in the methanol synthesis reactor, the synthesis gas and at least some of the carbon dioxide of the cooled gas stream under reaction conditions sufficient to produce methanol.

19. The method of claim 2, wherein reforming the natural gas comprises reacting the natural gas with water.

20. The method of claim 3, wherein reforming the natural gas comprises reacting the natural gas with water.

\* \* \* \* \*